United States Patent [19]

Sakurada et al.

[11] Patent Number: 4,536,369
[45] Date of Patent: Aug. 20, 1985

[54] AUTOMATIC ANALYZING APPARATUS

[75] Inventors: Masahiko Sakurada, Machida; Sugio Manabe, Kodaira; Hideaki Okamura, Kawasaki; Nagahiro Gocho, Hachioji, all of Japan

[73] Assignee: Olympus Optical Company Limited, Tokyo, Japan

[21] Appl. No.: 246,055

[22] Filed: Mar. 2, 1981

[30] Foreign Application Priority Data

Mar. 21, 1980 [JP] Japan .................. 55-36480

[51] Int. Cl.³ ............................................. G01N 35/02
[52] U.S. Cl. ..................................... 422/65; 356/433; 356/435; 364/499; 422/64; 422/67; 436/47; 436/164
[58] Field of Search ............................ 422/67, 64, 65; 356/433, 435; 364/497, 498; 436/47, 164

[56] References Cited

U.S. PATENT DOCUMENTS

| 2,554,414 | 5/1951 | McClendon | 422/91 |
| 3,526,480 | 9/1970 | Findl et al. | 422/66 |
| 4,059,405 | 11/1977 | Sodickson et al. | 23/230 R |
| 4,061,469 | 12/1977 | Du Bose | 422/67 X |
| 4,158,545 | 6/1979 | Yamashita et al. | 422/67 |
| 4,276,051 | 6/1981 | Ginsberg et al. | 422/64 |
| 4,313,735 | 2/1982 | Yamashita et al. | 422/67 X |
| 4,338,279 | 7/1982 | Orimo et al. | 422/65 |

Primary Examiner—Michael S. Marcus
Attorney, Agent, or Firm—Parkhurst & Oliff

[57] ABSTRACT

An automatic analyzing apparatus for automatically effecting chemical analysis on a sample of blood, urea or the like dependent on measurement items by measuring the light absorption degree of a reaction liquid through a reaction vessel, comprising a reaction liquid photometric unit, a photometric unit independent of the reaction light photometric unit and operative to measure beforehand the light absorption degree of the reaction vessel per se or the reaction vessel containing a reagent or dilute liquid, and means for correcting the light absorption degree of the reaction liquid measured at the reaction liquid photometric unit on the basis of the light absorption degree of the reaction vessel per se or the light absorption degree of the reaction vessel containing the reagent or dilute liquid measured at the independent photometric unit.

4 Claims, 3 Drawing Figures

4,536,369

AUTOMATIC ANALYZING APPARATUS

BACKGROUND OF THE INVENTION

1. Field of the Invention

This invention relates to an automatic analyzing apparatus for automatically effecting chemical analysis on a sample of blood, urea or the like.

2. Description of the Prior Art

In an automatic analyzing apparatus heretofore proposed, a sample and a reagent dependent on measurement items are distributed into a reaction vessel to be transferred along a given path to obtain a reaction liquid and the light absorption degree of the reaction liquid is measured through the reaction vessel. Such automatic analyzing apparatus for measuring the light absorption degree of the reaction liquid through the reaction vessel has the drawback that the irregular light absorption degree of the reaction vessel per se is influential to the analytical accuracy.

In order to obviate such drawback, another automatic analyzing apparatus has been proposed which can measure the light absorption degree of the reaction vessel prior to the analysis and correct the light absorption degree of the reaction liquid. Such automatic analyzing apparatus function to repeatedly wash and use a reaction vessel set beforehand to the apparatus and measure the light absorption degree of the reaction vessel and of the reaction liquid at the same photometric unit, thereby lowering the process ability of the apparatus. Particularly, the repeated use of the reaction vessel provides the disadvantage that the change of the light absorption degree of the reaction vessel due to the change of the physical condition such as contamination, damage or the like produced when the reaction vessel is repeatedly used and the change of the light absorption degree after the lapse of time could not be corrected. As a result, after the lapse of long times, the analytical accuracy of the apparatus becomes degraded. Particularly, the analytical accuracy of an analytical method which makes use of an end point process of measuring the light absorption degree of the reaction liquid on the basis of the light absorption degree of a reagent becomes considerably degraded.

Meanwhile, a further automatic analyzing apparatus has been proposed which can measure the light absorption degree of the reaction liquid through a reaction vessel which is disposable and discarded. In such apparatus, the reaction vessel is different for every one sample, so that the liquid absorption degrees of these reaction vessels are different from each other. The disposable reaction vessel is usually formed of light transmission plastics such as polymethyl pentene resin or the like whose slight change in size, dimension, material composition, shaping condition or the like makes the light absorption degree of the reaction vessel irregular. In order to limit such irregular light absorption degree within a given accuracy, use must be made of apparatus which is complex in construction, sensitive in operation and expensive.

SUMMARY OF THE INVENTION

An object of the invention, therefore, is to provide an automatic analyzing apparatus which can eliminate the above mentioned drawbacks which have been encountered with the prior art techniques, and which can always analyze desired measurement items in a highly precise manner without degrading the analytical process ability irrespective of repeated use of reaction vessel and of the use of disposable reaction vessels.

A feature of the invention is the provision in an automatic analyzing apparatus comprising a reaction vessel to be transferred along a given path, means for distributing a sample and a reagent or dilute liquid dependent on measurement items into the reaction vessel at desired positions of the path to obtain a reaction liquid and a reaction liquid photometric unit for measuring the light absorption degree of the reaction liquid through the reaction vessel to effect the quantitative analysis of the measurement items, of the improvement comprising a photometric unit independent of said reaction liquid photometric unit and located at a position in front of said sample distribution position and in front of or in the rear of said reagent or dilute liquid distribution position, and means for correcting the light absorption degree of the reaction liquid measured at said reaction liquid photometric unit on the basis of the light absorption degree of the reaction vessel per se or on the basis of the light absorption degree of the reaction vessel containing the reagent or dilute liquid measured at the independent photometric unit.

Further objects and features of the invention will be fully understood from the following detailed description with reference to the accompanying drawings, wherein:

DETAILED DESCRIPTION OF THE PREFERRED EMBODIMENTS

Figure 1:
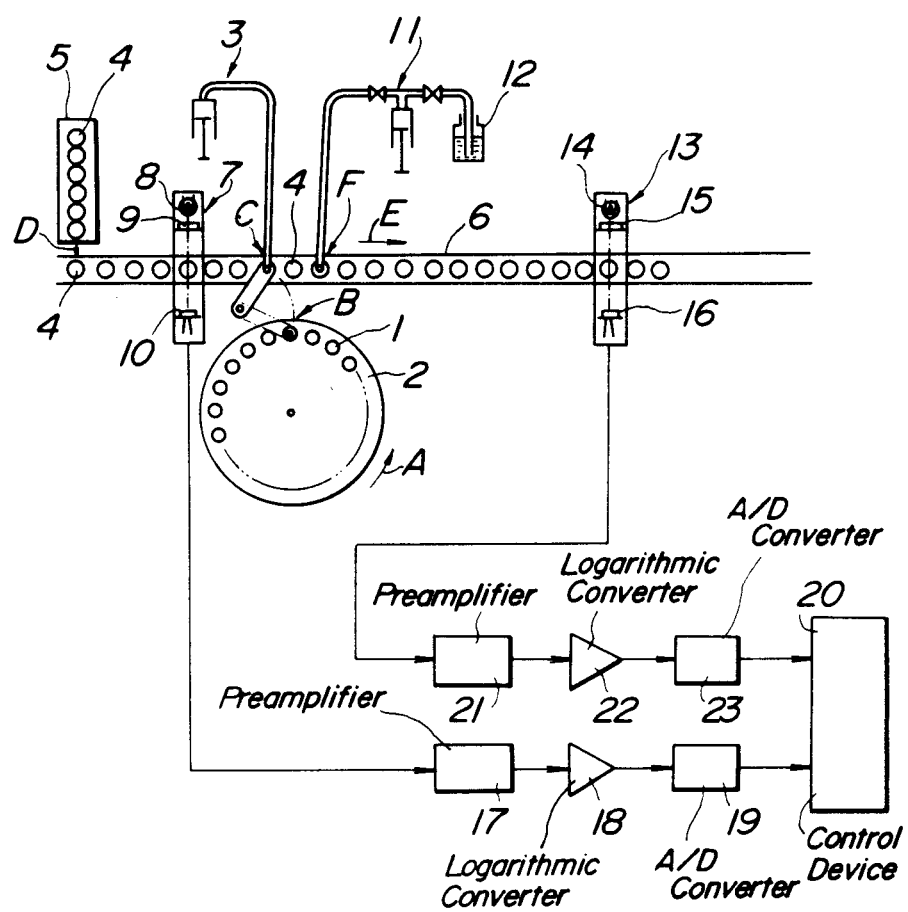
FIG. 1 is a diagrammatic view of one embodiment of an automatic analyzing apparatus according to the invention.

FIG. 1 shows one embodiment of an automatic analyzing apparatus according to the invention. The automatic analyzing apparatus is of a type which makes use of disposable reaction vessels. A plurality of sample vessels 1 containing various kinds of samples such as blood, urine or the like are held by a sample vessel transfer device 2 and intermittently rotated and transferred in a direction shown by an arrow A. A given amount of the sample in each sample vessel 1 is sucked at a given sample sucking position B into a reaction vessel 4 located at a distribution position C in succession by means of a sample distribution mechanism 3 in response to the number of measurment items. At a given position D, the reaction vessel 4 is supplied to a reaction vessel transfer mechanism 6 in succession by means of a reaction vessel supply mechanism 5. The reaction vessel 4 is held by the transfer mechanism 6 and is intermittently or continuously transferred along a given transfer path E including the sample distribution position C. In the present embodiment, at that position of the transfer path E which lies between the reaction vessel supply position D and the sample distribution position C is arranged a reaction vessel photometric unit 7 for measuring the light absorption degree of the reaction vessel 4 per se. The photometric unit 7 is composed of a white color light source 8, an interference filter 9 irradiated with light emitted from the white color light source and delivering a light having a given wave length and a photoelectric conversion element 10 operative to receive a light transmitted through the reaction vessel 4.

The reaction vessel 4 containing the sample distributed therein is further transferred along the transfer path E and arrives at a given position F where a reagent distribution mechanism 11 functions to distribute the reagent dependent on the measurement item into the reaction vessel 4. In FIG. 1 is shown only one reagent container 12, but use may be made of a plurality of reagent containers 12 for the purpose of distributing the reagents dependent on the measurement items into the reaction vessel 4 by means of the reagent distribution mechanism 11. The sample and reagent distributed into the reaction vessel 4 are mixed and reacted with each other at a constant temperature in the course of transfer step along the transfer path E. The reaction liquid thus obtained arrives at a reaction liquid photometric unit 13 arranged at a given position of the transfer path E and measuring the light absorption degree of the reaction liquid through the reaction vessel 4. The reaction liquid photometric unit 13 is composed of a white color light source 14, an interference filter 15 and a photoelectric conversion element 16 in the same manner as the above mentioned reaction vessel photometric unit 7.

The reaction vessel 4 which has passed through the reaction liquid photometric unit 13 is removed out of the reaction vessel transfer mechanism 6 by means of a suitable discarding means not shown.

The photoelectric signal delivered from the reaction vessel photometric unit 7 shown in FIG. 1 is amplified by a preamplifier 17 and then supplied through a logarithmic converter 18 and A/D converter 19 to a control device 20 including a computer by which the photoelectric signal is memorized. Similarly, the photoelectric signal delivered from the reaction liquid photometric unit 13 is supplied through a preamplifier 21, logarithmic converter 22 and A/D converter 23 to the control device 20. In the control device 20, the light absorption degree of the reaction liquid is corrected on the basis of the light absorption degree of the corresponding reaction vessel memorized beforehand by the control device 20. The light absorption degree value thus corrected is displayed on a display device not shown or printed out on a printer. The apparatus is constructed such that the control device 20 functions to control on the basis of sample informations received the operation of the above mentioned sample transfer mechanism 2, sample distribution mechanism 3, reaction vessel transfer mechanism 6, reaction vessel photometric unit 7, reagent distribution mechanism 11, reaction liquid photometric unit 13 or the like.

In the present embodiment, prior to the distribution of the sample and reagent into the reaction vessel 4, the reaction vessel photometric unit 7 independent of the reaction liquid photometric unit 13 functions to measure beforehand the light absorption degree of respective reaction vessels 4 in succession. As a result, the irregular light absorption degree of the reaction vessel can effectively be corrected so as to effect a highly precise analysis. In addition, the irregular light absorption degree of the reaction vessel 4 is not required to be kept within a given accuracy, so that the apparatus can easily be manufactured in a less expensive manner.

Figure 2:
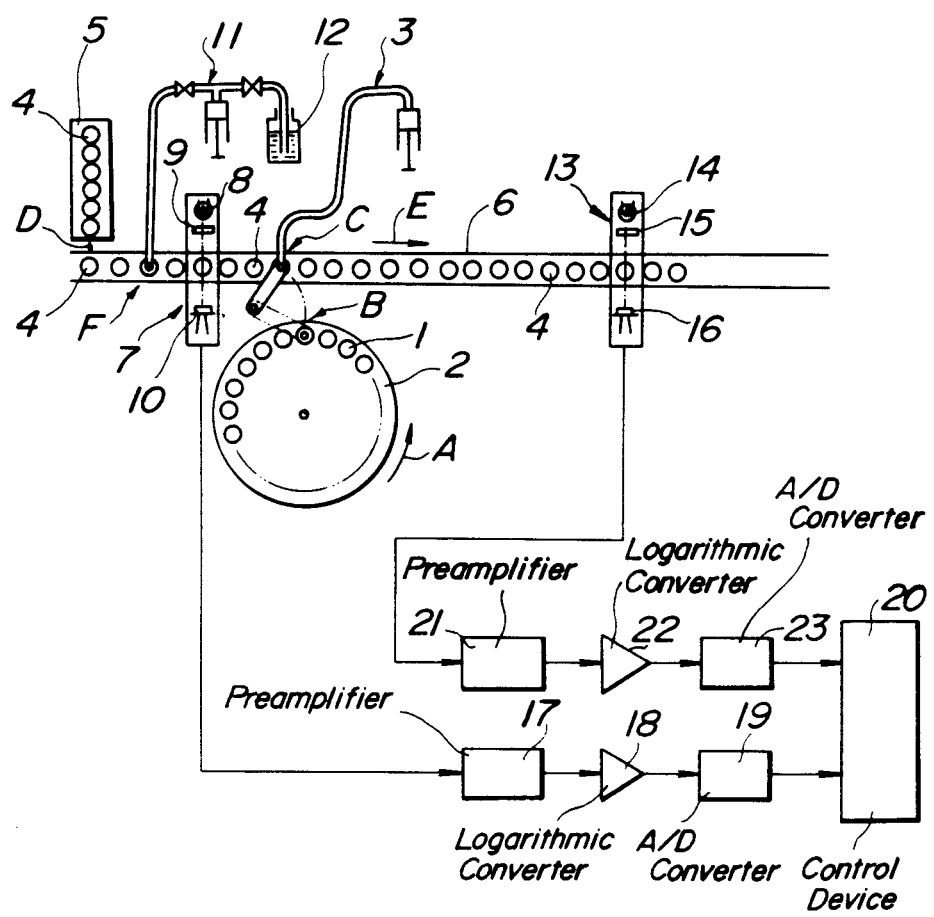
FIG. 2 is a diagrammatic view of another embodiment of an automatic analyzing apparatus according to the invention.

FIG. 2 shows another embodiment of an automatic analyzing apparatus according to the invention. In the present embodiment, a reagent distribution position F is not located in the rear of a sample distribution position C, but is located in front of the sample distribution position C and between a reaction vessel supply position D and a reaction vessel photometric unit 7. The same reference numerals in FIG. 2 as those shown in FIG. 1 designate the same parts as those shown in FIG. 1.

In the embodiment shown in FIG. 2, after a given reagent has been distributed into the reaction vessel 4, the light absorption degree of the reagent is measured prior to distribution of the sample into the reaction vessel 4 by a photometric unit 7 independent of the reaction liquid photometric unit 13. As a result, it is possible to effectively correct not only the light absorption degree of the reaction vessel 4 per se but also the change in the light absorption degree of the reagent due to the change with the lapse of time. Thus, the apparatus can effect analysis in a highly precise manner. In addition, it is possible to manufacture the reaction vessel 4 in an easy and less expensive manner.

Figure 3:
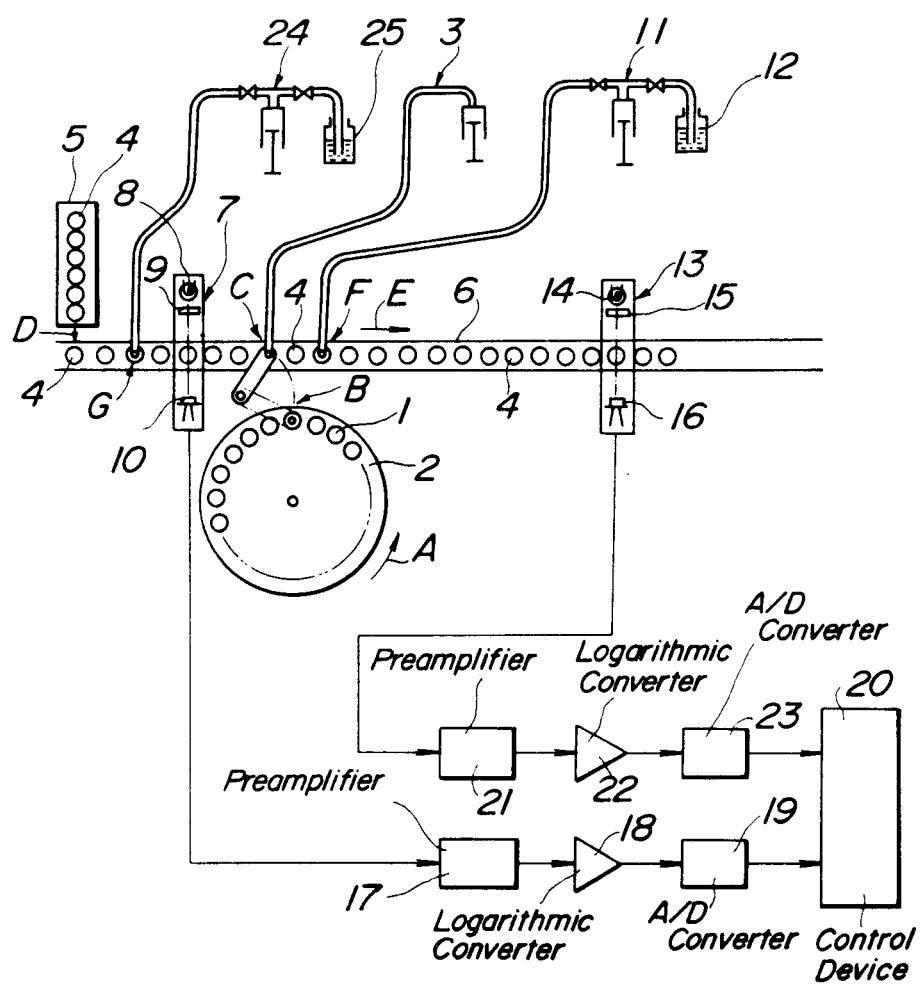
FIG. 3 is a diagrammatic view of a further embodiment of an automatic analyzing apparatus according to the invention.

FIG. 3 shows a further embodiment of an automatic analyzing apparatus according to the invention. In the present embodiment, at that position of the transfer path E which lies between the reaction vessel supply position D and the reaction vessel photometric unit 7 is located a dilute liquid distribution position G where the dilute liquid in a container 23 is distributed into the reaction vessel 4 by means of a dilute liquid distribution mechanism 24. The same reference numerals in FIG. 3 as those shown in FIG. 1 designate the same parts as those shown in FIG. 1. In the automatic analyzing apparatus, the sample or concentrated reagent may be diluted and distributed. In the present embodiment, the dilute solution is distributed beforehand into the reaction vessel 4 prior to the distribution of the sample and reagent thereinto and the light absorption degree of the reaction vessel 4 distributed beforehand with the dilute liquid thereinto is measured by means of a photometric unit 7 independent of a reacted liquid photometric unit 13. As a result, the present embodiment can effectively correct the irregular light absorption degree of the reaction vessel 4 in a manner similar to the previous embodiments. In addition, measuring the light absorption degree of the reaction vessel 4 containing the dilute liquid ensures a decrease of the difference between refractive indexes at boundary surfaces having different refractive indexes and provides the important advantage that correction can be effected under the condition which is closer to the case of practically measuring the reaction liquid than the case of measuring a vacant reaction vessel. Thus, it is possible to effect the desired analysis in a more precise manner.

The invention is not limited to the above mentioned embodiments only, but various changes and alterations are possible. For example, provision may be made for a plurality of sample distribution positions C and reaction liquid photometric units 13, if desired. In addition, in the automatic analyzing apparatus shown in FIGS. 1 and 3, the sample distribution position C and the reagent distribution position F may be reversed in position or these positions may be located at the same position. In the case of distributing different reagents in succession, a first reagent may be distributed into the reaction vessel at the dilute liquid distribution position G shown in FIG. 3 and second reagent may be distributed into the reaction vessel at the reagent distribution position F. The invention may be effectively applied not only to the automatic analyzing apparatus which makes use of the disposable reaction vessel, but also to the automatic analyzing apparatus which repeatedly makes use of the same reaction vessel.

As stated hereinbefore, in the automatic analyzing apparatus according to the invention, provision is made of a photometric unit independent of the reaction liquid photometric unit and operative to measure beforehand the absorption degree of the reaction vessel per se or the reaction vessel containing the reagent or dilute liquid and the light absorption degree of the reaction liquid is corrected on the basis of the light absorption degree thus measured. Thus, the automatic analyzing apparatus according to the invention can effect the analysis in a highly precise manner without degrading the analytical process ability.

What is claimed is:

1. An automatic analyzing apparatus comprising means for transferring a reaction vessel along a given traveling path in a stepwise manner pitch by pitch;
   means arranged on the traveling path at a reagent distribution position for distributing a reagent corresponding to a measurement item to be tested into the reaction vessel transferred into the reagent distribution position;
   means arranged on the traveling path at a sample distribution position which is downstream with respect to said reagent distribution position, said sample being distributed into the reaction vessel to form a reaction liquid;
   a first photometric unit arranged on the traveling path at a position between the reagent distribution position and the sample distribution position for measuring an absorption degree of the reaction vessel and the reagent contained in the reaction vessel;
   a second photometric unit arranged on the traveling path at a downstream position with respect to said sample distribution position for measuring an absorption degree of the reaction liquid through the reaction vessel;
   means for correcting the absorption degree of the reaction liquid on the basis of the absorption degree of the reaction vessel and the reagent to derive a corrected absorption degree of the reaction liquid alone;
   means arranged on the traveling path at an upstream position with respect to said reagent distribution position for supplying new reaction vessels onto the reaction vessel transferring means; and
   means arranged on the traveling path at a downstream position with respect to the second photometric unit for removing the reaction vessels containing the reaction liquids from the traveling path.

2. An apparatus according to claim 1, wherein said traveling path along which the reaction vessels are transferred is formed rectilinearly.

3. An apparatus according to claim 1, wherein each of said first and second photometric units comprises a white color light source, interference filters irradiated with light emitted from the white color light source and delivering a light having a given wave length and a photoelectric conversion element operative to receive said light transmitted through the reaction vessel.

4. An apparatus according to claim 1, wherein said means for correcting the light absorption degree of the reaction liquid comprises a control device including a memory for storing the absorption degree of the reagent and an electronic computer connected to respective photometric units.

* * * * *